United States Patent
Ng et al.

(10) Patent No.: US 7,400,407 B2
(45) Date of Patent: Jul. 15, 2008

(54) METER FOR MEASURING THE TURBIDITY OF FLUIDS USING REFLECTED LIGHT

(75) Inventors: Joh Joh Ng, Perak (MY); Khee Boon Lim, Penang (MY); Chee Wai Chia, Penang (MY); Selvan Maniam, Pulau Pinang (MY)

(73) Assignee: Avago Technologies ECBU IP Pte Ltd, Singapore (SG)

( * ) Notice: Subject to any disclaimer, the term of this patent is extended or adjusted under 35 U.S.C. 154(b) by 323 days.

(21) Appl. No.: 11/216,476

(22) Filed: Aug. 31, 2005

(65) Prior Publication Data

US 2007/0046942 A1    Mar. 1, 2007

(51) Int. Cl.
*G01N 21/00*  (2006.01)
(52) U.S. Cl. .................. 356/442; 356/441; 356/439
(58) Field of Classification Search ........... 356/300, 356/317, 423–444
See application file for complete search history.

(56) References Cited

U.S. PATENT DOCUMENTS

| | | | | |
|---|---|---|---|---|
| 3,114,253 A | * | 12/1963 | Morey et al. | 68/12.02 |
| 3,870,417 A | * | 3/1975 | Bashark | 356/442 |
| 3,888,269 A | * | 6/1975 | Bashark | 134/57 D |
| 4,152,070 A | * | 5/1979 | Kushner et al. | 356/343 |
| 4,263,511 A | * | 4/1981 | Hirschberg | 250/343 |
| 5,350,922 A | * | 9/1994 | Bartz | 250/338.5 |
| 5,510,620 A | * | 4/1996 | Achter et al. | 250/339.12 |
| 5,560,060 A | * | 10/1996 | Dausch et al. | 8/158 |
| 5,586,567 A | * | 12/1996 | Smith et al. | 134/57 D |
| 5,731,868 A | * | 3/1998 | Okey et al. | 356/73 |
| 5,806,541 A | * | 9/1998 | Cooper et al. | 134/57 D |
| H1783 H | * | 2/1999 | McLean | 356/5.04 |
| 6,028,694 A | * | 2/2000 | Schmidt | 359/264 |
| 6,190,609 B1 | * | 2/2001 | Chapman et al. | 422/24 |
| 6,864,985 B1 | * | 3/2005 | Tanzer | 356/446 |
| 2004/0135089 A1 | | 7/2004 | Manz et al. | |

FOREIGN PATENT DOCUMENTS

WO    WO 00/71994 A1 * 11/2000

* cited by examiner

*Primary Examiner*—Gregory J. Toatley, Jr.
*Assistant Examiner*—Jarreas Underwood

(57) ABSTRACT

A meter for measuring the turbidity of a fluid includes a light source for directing a light beam through a fluid under test towards a reflective surface and a sensor for detecting light reflected from the reflective surface and passing back through the fluid under test. The meter outputs a signal indicative of the turbidity of the fluid under test.

20 Claims, 2 Drawing Sheets

METER FOR MEASURING THE TURBIDITY OF FLUIDS USING REFLECTED LIGHT

BACKGROUND OF THE INVENTION

Modern homes are filled with sensors. They are used extensively in many major appliances such as washing machines, cloths dryers, dishwashers, water heaters, refrigerators, freezers, ovens and microwave ovens. Growth in the home appliance sensor market is being fueled by end-user demand for smarter and more compact products. Meeting this need has been possible with the development of more compact, accurate, efficient and reliable photo-sensors for replacing conventional mechanical sensors which are generally bulkier, less accurate, less efficient and less reliable.

Advances in color sensors are also helping to meet this need for sensors in appliances. Here, color sensor is defined as a sensor that can simultaneously detect and identify multiple colors. Color sensors can be inexpensive, compact and allow for convenient interfaces with modern control systems. They provide superior readings, enable faster data acquisition and provide more reliable data on the operating conditions of appliances.

U.S. patent application Publication No. U.S. 2004/0135089 to Manz et al. describes a transmission sensor. The sensor measures the turbidity of a liquid by shining light along two paths. One of the paths is a longer path and is detected by a first receiver. The other path is a shorter path and is detected by a second receiver. The light is directly transmitted from a light transmitter, through the fluid media, to the receivers.

FIG. 1 shows another prior-art transmissive device 101 for measuring the turbidity of a liquid media 103, for example dyed water or cloudy water, whereby light 105 is directly transmitted from a phosphor white LED light source 107, through the liquid 103, to a color sensor 109.

The light source 107 and the color sensor 109 are mounted opposite and perpendicularly to each other with a transparent cavity 111 placed between them. The light source 107 illuminates the cavity 111 and the optical characteristics of the transmitted light 105 are determined by the liquid 103 in the cavity.

The liquid 103 can act as a filter. For example, the transmitted light 105 received by the color sensor 109 will appear bluish if the liquid is bluish. That is because the bluish liquid mainly passes the blue light component and absorbs most of the rest.

In an appliance such as a washing machine, the luminance/intensity and chromaticity/color information of light exiting from the fluid is used to determine if any discoloration or contamination has occurred.

However, the transmission sensor described in FIG. 1 has several disadvantages.

The design is very bulky. As shown in FIG. 1, the light source 107 is mounted opposite to the light sensor 109. Therefore, the setup takes up more space and is not practical for applications where space is critical.

The design is complicated and requires difficult routing. The relative positioning between the light source 107, cavity 111 and light sensor is critical and even a slight displacement will affect the accuracy of the result. If, for example, the light sensor 109 is not aligned with the light source 107, the transmitted light 105 detected will not be able to indicate the level or contamination or discoloration correctly.

The transmission sensor design also does not have very good sensitivity for measuring fluids with low contamination or discoloration levels. For a given apparatus size, the transmitted light beam 105 only passes through the liquid 103 once with the effective beam path equal to the distance "d". The signal attenuation caused by the low contamination level is not able to give a significant or accurate measurement of how discolored or contaminated the liquid is.

The transmission sensor of Manz et al. described above has these same disadvantages and additionally makes no use of modern color sensors or color data.

It would be desirable to have a meter for measuring the turbidity of fluids that is compact, simple to manufacture and has good sensitivity for measuring fluids having low turbidity.

SUMMARY OF THE INVENTION

A meter for measuring the turbidity of a fluid includes a light source for directing a light beam through a fluid under test towards a reflective surface and a sensor for detecting light reflected from the reflective surface and passing back through the fluid under test. The meter outputs a signal indicative of the turbidity of the fluid under test.

Other aspects and advantages of the present invention will become apparent from the following detailed description, taken in conjunction with the accompanying drawings, illustrated by way of example of the principles of the invention.

DETAILED DESCRIPTION

Figure 2:
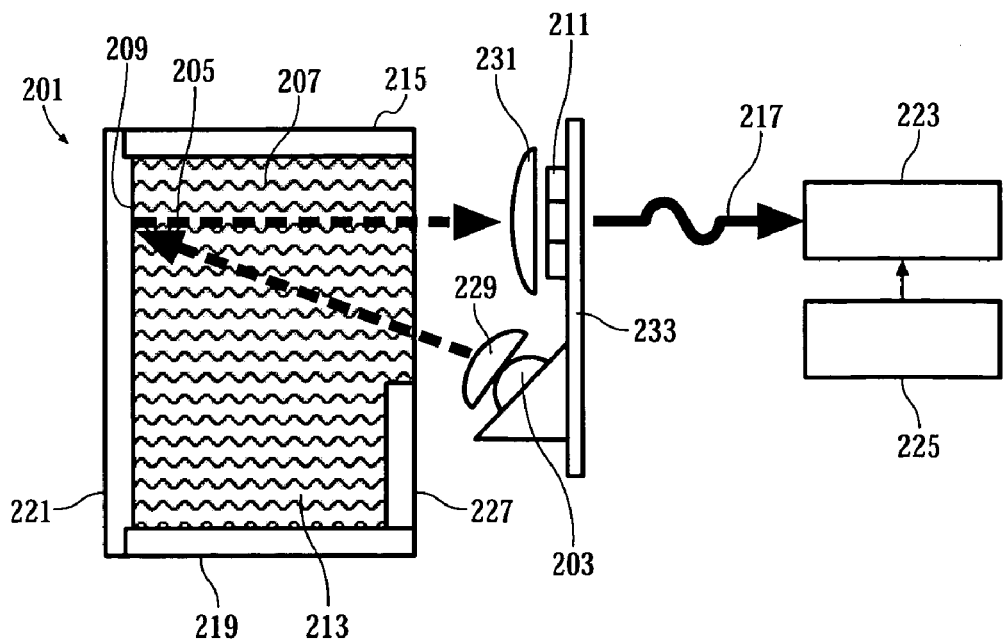
FIG. 2 shows a first embodiment of a meter for measuring the turbidity of a fluid under test of the present invention.

FIG. 2 shows a first embodiment of a meter 201 for measuring the turbidity of a fluid under test 207 of the present invention. A light source 203 emits a light beam 205 which passes through the fluid under test 207, reflects from a reflective surface 209, passes through the fluid under test 207 again and is then detected by a light sensor 211, which can be a multi-band sensor, or more specifically a color sensor.

Figure 1:
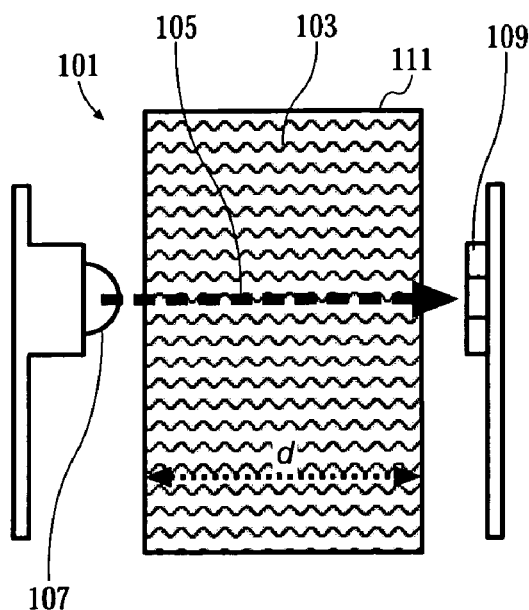
FIG. 1 shows a prior-art transmissive device for measuring the turbidity of a liquid media.

The present invention uses reflected light as opposed to using directly transmitted light as does US Patent Application Publication Number US 2004/0135089 to Manz et al. and the prior-art described in FIG. 1. The result is a meter 201 for measuring the turbidity of the fluid under test 207 which is compact, simple to manufacture and has good sensitivity for measuring fluids having even a low turbidity.

Figure 3:
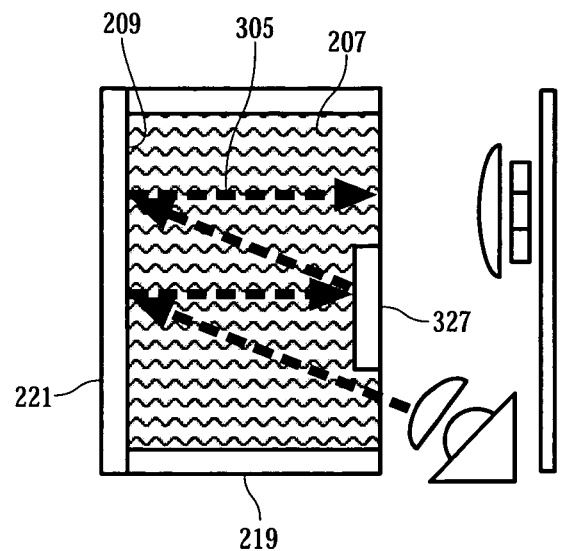
FIG. 3 shows a multiple-reflection embodiment of a meter for measuring the turbidity of a fluid under test of the present invention.

The meter 201 is more compact than the prior-art device described in FIG. 1 as both the light source 203 and light sensor 211 are on the same side of the fluid under test 207 which is contained by the transparent cavity 213. This also results in a more economical and simpler mechanical design. The light beam 205 passes through the fluid under test 207 twice before being detected, rather than a single time, as it does in the prior-art, therefore resulting in a more sensitive measurement. The light beam 205 can also pass through the fluid under test 207 more than twice, as illustrated in the embodiment of FIG. 3, resulting in even greater sensitivity.

In the present invention, "light" is defined in the broad sense to mean "electromagnetic radiation of any wavelength". The definition of "light" should not be limited to the narrower definition of "light" as "electromagnetic radiation that has a wavelength in the range from about 4,000 (violet) to about 7,700 (red) angstroms and may be perceived by the normal unaided human eye." Thus, the light source 203 can produce, the light sensor 211 can detect, and the light beam 205 can, in the broadest definition of the invention, be "electromagnetic radiation of any wavelength" for a desired application.

The invention is now described in greater detail. Referring again to the first embodiment illustrated in FIG. 2, the light source 203 directs the light beam 205 through the fluid under test 207 towards the reflective surface 209.

The light source can produce white light or other wavelengths, broad or narrow spectrum, depending on the desired application. There are many available sources of white light. One example is a phosphor converted white LED comprised of a blue emitter together with yellow phosphor. This type of LED produces white by converting some of the blue light using the phosphor and then combining the converted light with some of the original blue light. Another example of a white LED uses a UV emitter to stimulate phosphor to produce white light. Any suitable color combinations of LED radiation and fluorescent material radiation may be used to achieve the desired purpose and effect. For example, a UV or green LED may be used. Also, a fluorescent material that emits green or red may be used. Any suitable color combinations are within the scope of the present invention. By the same token, a combination of Red, Green and Blue emitters can also be used to produce the desired white light. There are many available sources of white light, such as a phosphor white LED.

One specific example of a phosphor white LED light source is the AGILENT HLMP-CW78, HLMP-CW79, T-1 ¾Precision Optical Performance White LED available from the assignee of the present invention. This high intensity white LED lamp is based on InGaN material technology. A blue LED die is coated by phosphor to produce white. The typical resulting color is described by the coordinates x=0.32, y=0.32 using the 1931 CIE Chromaticity Diagram.

The fluid can be either a liquid or a gas. It will typically be turbid water of a household appliance such as dirty water in a washing machine or dishwasher. The fluid can also be the hydraulic oil or lubricant oil in an oil system. Water content in oil causes turbidity, in particular in the infrared range, and it is possible to monitor the water content in oil by measuring this turbidity. The fluid can also be air with smoke or other contaminants. These are just examples of possible fluids that can be examined with the present invention and are not meant to be limiting.

The light sensor 211 detects light beam 205 which is reflected from the reflective surface 209 and passed back through the fluid under test 207. The light sensor then outputs a signal 217 indicative of the turbidity of the fluid under test 207. The light sensor 211 can be a multi-band sensor. For example, it can use tri-band photodiodes that are coated with RGB filters. Alternatively, depending on application and accuracy needs, it can also use multi-band photodiodes that are coated with RGBCMY filters. The sensor can also be in the form of a multiple band color sensor such as RGBCMY color sensor.

The light sensor 211 can, for example, be the AGILENT HDJD-S722-QR999 color sensor, available from the assignee of the present invention, which can detect the presence of a certain color and identify its exact coordinate across the full color spectrum. It is available in a quad flat no-lead (QFN) package that measures a mere 5 mm×5 mm×1 mm. This miniature size simplifies printed-circuit-board design and provides the designer with greater flexibility in designing space-constrained applications. The RGB color sensor is comprised of a photodiode array coated with red, green and blue color filters and three trans-impedance amplifiers—all integrated in a single monolithic CMOS IC.

A light sensor which detects electromagnetic radiation outside of the visible range can also be used. For example, the sensor might detect infrared or ultraviolet radiation. The light sensor can be one that detects any portion of the spectrum from infrared to ultraviolet, depending on the particular fluid under test 207. The light source can produce white light or light anywhere within the portion of the spectrum from infrared to ultraviolet. It is often beneficial to choose the light sensor's portion of the spectrum to roughly correspond to the light source's portion of the spectrum. However, in some cases the light source can stimulate the fluid under test 207 to emit wavelengths covering a portion of the spectrum different than that of the light source. In this case it is beneficial to choose the light sensor's portion of the spectrum to correspond to the emitted wavelengths rather than the portion of the spectrum produced by the light source.

The light sensor 211 output signal 217 may take the form of analogue (photocurrent or voltage), digital or standard color space format.

The reflective surface 209 can form part of the walls 215 of a transparent cavity 213. Note that the reflective surface 209 does not need to be completely contiguous, but can be made up of several separate sections. The transparent cavity 213 includes side walls 219 a back wall 221, and a front wall 227. The back wall can be defined as the wall at which the light directly emitted from the light source is aimed and opposite the light source and sensor. The side walls 219 can be connected to and perpendicular to the back wall 221. The front wall 227 can be opposite to the back wall, on the side of the cavity closer to the source 223 and sensor 211. Of course the cavity 213 can have fewer or additional walls and can be of many different shapes. The reflective surface covers at least part of the side walls and back wall. The reflective side walls aid in channeling or focusing the light from the transparent cavity 213 to the sensor 211. The transparent cavity 213 contains the fluid under test 207. The reflective surface should be such that it reflects electromagnetic radiation of the frequency desired to be detected by the sensor 211. For example, in an application where it is desired to detect color light, the reflective surface can be a mirror. On the same token, the reflective surface can be composed of any material as long as it serves the purpose of reflecting light.

FIG. 3 shows another embodiment of the present invention including a front wall 327 which is also covered at least in part by the reflective surface 209. Note that the front, back or side walls themselves can also be the reflective surface 209. The light beam 305 is reflected between the front and back wall before being focused onto the sensor. The light beam 305 is illustrated passing through the fluid under test 207 four times, providing more interaction between the light beam and the fluid under test, thereby resulting in even greater sensitivity. In other configurations the light beam 305 can be aimed to be reflected from the back wall 221 to the front wall 327 and back to the back wall 221 more than once and to thus pass through the fluid even more than four times.

The sensor outputs a signal 217 indicative of the turbidity of the fluid under test 207. Here, turbidity is defined broadly.

Thus, the fluid is turbid if it has mixed in sediment or foreign particles. The fluid can be a gas or a liquid. Thus, water is turbid if it has dirt, soap, dye, or any other type of sediment or foreign particles mixed or dissolved in. Oil having water mixed into it is also turbid. Air with pollutants mixed in is turbid as well. Turbidity provides a measurement of the amount of mixed in sediment or foreign particles in the fluid.

A processor (or processing circuitry) 223 can compare the signal 217 to a reference signal 225 to determine the change in turbidity relative to the turbidity indicated by the reference signal 225. The reference signal 225 can be output from the color sensor by filling the transparent cavity 213 with a reference fluid prior to filling it with the fluid under test 207. Alternatively, the reference signal 225 can be pre-stored for access by the processor 223. The reference signal 225 can represent the light received by the sensor 211 when passing through the fluid under test 207 before the turbidity is introduced into the fluid under test 207, for example. Thus, if the invention is used in a washing machine, the light sensor output for original clean water and dirty water can be compared to identify the level of water contamination or turbidity. The light sensor output can also be analyzed to determine the type of contamination in the water.

The signal 217 contains information indicative of the turbidity of the fluid under test. The optical characteristics of the reflected light will be greatly determined by the luminance, chromaticity and saturation level of the fluid under illumination. For instance, a bluish fluid will allow a blue component to pass directly through to the sensor or to be reflected from the sidewalls to the sensor, while blocking other components. The optical characteristics of the reflected light will be converted to photocurrent by the sensor and the output signal can be in either current or voltage format. In addition to analog format, the output can be digital format or standard color space format, for example. The processing circuitry receives the signal and determines the turbidity of the fluid under test based on the luminance, chromaticity or saturation level of the detected light.

As shown in FIGS. 2 and 3, the light source 203 and sensor 211 can be mounted on a common planer carrier 233 such as a PC board. This results in cheaper manufacturing and more convenient alignment than in the prior-art. Alternatively, the source and sensor can be mounted on a substrate. In some embodiments the source and sensor might be unpackaged diodes mounted directly on a substrate.

The light source 203 directs the light at a non-perpendicular angle relative to the back wall 221 so that light reflected from the back wall 221 is received by the sensor 211. In the embodiments illustrated in both FIGS. 2 and 3 the angle of the source can be chosen to optimize the reflected light reaching the sensor.

The invention can also include a first optical lens 229 positioned between the light source 203 and the reflective surface 209 for focusing the light 205 through the fluid under test 207. A second optical lens 231 is positioned between the reflective surface 209 and the sensor 211 for focusing the reflected light 205 onto the sensor 211.

Figure 4A:
FIG. 4a shows a washing machine using the meter of the present invention to determine the turbidity of water in the washing machine during a wash cycle.

There are many possible applications for the meter for measuring the turbidity of a fluid of the present invention. FIG. 4a shows a washing machine 401 using the meter 201 of the present invention to determine the turbidity of water in the washing machine during a wash cycle. Clean water is added to a drum of the washing machine when the meter for measuring turbidity determines that the turbidity is above a threshold level. Also, the washing cycle may be shortened or extended to ensure optimum efficiency and cleanliness depending on the measured turbidity.

Figure 4B:
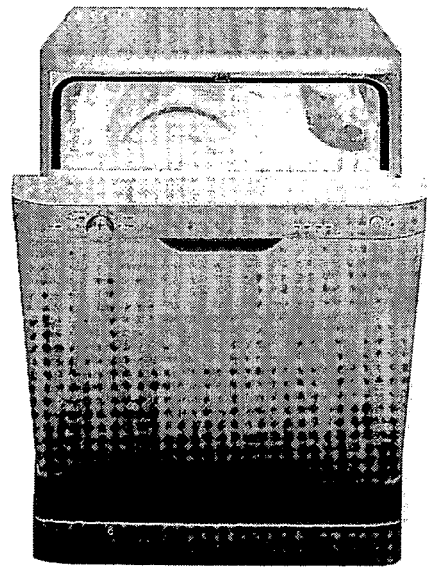
FIG. 4b shows a dishwasher using the meter of the present invention to determine the turbidity of water in the dishwasher during a wash cycle.

FIG. 4b shows a dishwasher 403 using the meter 201 of the present invention to determine the turbidity of water in the dishwasher during a wash cycle. Clean water is added to a tub of the dishwasher when the meter for measuring turbidity determines that the turbidity is above a threshold level.

Although specific embodiments of the invention have been described and illustrated, the invention is not to be limited to the specific forms or arrangements of parts so described and illustrated. The scope of the invention is to be defined by the claims appended hereto and their equivalents.

What is claimed is:

1. A meter for measuring the turbidity of a fluid comprising:
    a light source for directing a light beam through a fluid under test towards a reflective surface;
    a sensor for detecting light reflected from the reflective surface and passing back through the fluid under test and outputting a signal indicative of the turbidity of the fluid under test, and
    transparent cavity for containing the fluid under test;
    wherein the reflective surface is formed on side walls and a back wall of the transparent cavity.

2. The meter for measuring turbidity of claim 1, wherein the sensor is a color sensor.

3. The meter for measuring turbidity of claim 1, wherein the sensor is a multiband sensor.

4. The meter for measuring turbidity of claim 1, wherein the sensor separately and simultaneously detects multiple wavelengths of electromagnetic radiation.

5. The meter for measuring turbidity of claim 1, wherein the light source is a phosphor white LED.

6. The meter for measuring turbidity of claim 1, wherein the light source is a combination of multiple wavelength LEDs.

7. The meter for measuring turbidity of claim 1, wherein the light source directs the light at a non-perpendicular angle relative to the back wall so that light reflected from the back wall is received by the sensor.

8. The meter for measuring turbidity of claim 1, wherein the signal is compared to a reference signal to determine the change in turbidity relative to the turbidity indicated by the reference signal.

9. The meter for measuring turbidity of claim 8, wherein the reference signal is output from a color sensor by filling the transparent cavity with a reference fluid prior to filling it with the fluid under test.

10. The meter for measuring turbidity of claim 1, wherein the reflective surface is additionally comprised of a front wall and light is reflected between the front and back wall before being focused onto the sensor.

11. The meter for measuring turbidity of claim 1, wherein the side walls channel the reflected light onto the sensor.

12. The meter for measuring turbidity of claim 1, further comprising a first optical lens positioned between the light source and the reflective surface for focusing the light through the fluid under test and a second optical lens positioned between the reflective surface and the sensor for focusing the reflected light onto the sensor.

13. The meter for measuring turbidity of claim 1, wherein the light source and sensor are mounted on a common planar carrier.

14. The meter for measuring turbidity of claim 1, wherein the signal contains luminance information indicative of the turbidity of the fluid under test and further comprising processing circuitry, the processing circuitry receiving the signal and determining the turbidity of the fluid under test based on the luminance of the detected light.

15. The meter for measuring turbidity of claim 1, wherein the signal contains chromaticity information indicative of the turbidity of the fluid under test and further comprising processing circuitry, the processing circuitry receiving the signal and determining the turbidity of the fluid under test based on the chromaticity of the detected light.

16. The meter for measuring turbidity of claim 1, wherein the signal contains saturation level information indicative of the turbidity of the fluid under test and further comprising processing circuitry, the processing circuitry receiving the signal and determining the turbidity of the fluid under test based on the saturation level of the detected light.

17. A washing machine using the meter of claim 1 to determine the turbidity of water in the washing machine during a wash cycle.

18. The washing machine of claim 17, wherein clean water is added to a drum of the washing machine when the meter for measuring turbidity determines that the turbidity is above a threshold level.

19. A dishwasher using the meter of claim 1 to determine the turbidity of water in the dishwasher during a wash cycle.

20. The dishwasher of claim 19, wherein clean water is added to a tub of the dishwasher when the meter for measuring turbidity determines that the turbidity is above a threshold level.

* * * * *